United States Patent
Kang et al.

(10) Patent No.: US 10,197,865 B2
(45) Date of Patent: Feb. 5, 2019

(54) LIQUID CRYSTAL DISPLAY AND MANUFACTURING METHOD THEREOF

(71) Applicant: Samsung Display Co., Ltd., Yongin-si, Gyeonggi-do (KR)

(72) Inventors: Suk Hoon Kang, Seoul (KR); Hoi-Lim Kim, Seoul (KR); Jong Hwan Jeon, Hwaseong-si (KR); Jin-Soo Jung, Hwaseong-si (KR); In Ok Kim, Osan-si (KR); Baek Kyun Jeon, Yongin-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 394 days.

(21) Appl. No.: 15/003,841

(22) Filed: Jan. 22, 2016

(65) Prior Publication Data

US 2017/0023832 A1 Jan. 26, 2017

(30) Foreign Application Priority Data

Jul. 24, 2015 (KR) ........................ 10-2015-0105257

(51) Int. Cl.
*G02F 1/1337* (2006.01)
*C07D 487/04* (2006.01)
*C07D 207/452* (2006.01)

(52) U.S. Cl.
CPC ... *G02F 1/133788* (2013.01); *C07D 207/452* (2013.01); *C07D 487/04* (2013.01); *G02F 1/133711* (2013.01); *G02F 2001/133738* (2013.01)

(58) Field of Classification Search
None
See application file for complete search history.

(56) References Cited

U.S. PATENT DOCUMENTS

| | | | |
|---|---|---|---|
| 6,063,829 A | 5/2000 | Endou et al. | |
| 7,456,141 B2 | 11/2008 | Hsu et al. | |
| 2014/0368779 A1* | 12/2014 | Park | G02F 1/133723 349/124 |
| 2016/0244673 A1* | 8/2016 | Kunimi | G02F 1/133723 |

FOREIGN PATENT DOCUMENTS

| | | | | |
|---|---|---|---|---|
| JP | 2008116809 | | 5/2008 | |
| JP | 201293642 | | 5/2012 | |
| JP | 2014199332 | | 10/2014 | |
| KR | 1020120082413 | | 7/2012 | |
| KR | 1020140146522 | | 12/2014 | |
| WO | WO-2015060363 A1 * | | 4/2015 | G02F 1/133723 |

* cited by examiner

*Primary Examiner* — Shamim Ahmed
*Assistant Examiner* — Bradford M Gates
(74) *Attorney, Agent, or Firm* — Cantor Colburn LLP

(57) ABSTRACT

A manufacturing method of a liquid crystal display, including: applying a photoalignment agent on a substrate; baking the applied photoalignment agent; forming a photoalignment layer by irradiating the baked photoalignment agent with polarized light; baking the photoalignment layer; and removing at least one decomposed unit by cleaning the baked photoalignment layer using a cleaning solution including at least one of propylene glycol monomethyl ether, propylene glycol monomethyl ether acetate, or ethyl lactate.

16 Claims, 6 Drawing Sheets

FIG. 6

| | 2nd Bake | | PGME | EL | PGMEA | IPA |
|---|---|---|---|---|---|---|
| | Temp. (°C) | Time (min) | | | | |
| 70 °C HTS Exposure 0.5 J | 220 | 15 | 500 h | 500 h | 500 h | 0 h |
| | | 30 | 500 h | 500 h | 500 h | 24 h |
| | 230 | 15 | 500 h | 500 h | 500 h | 0 h |
| | | 30 | 500 h | 500 h | 500 h | 24 h |

LIQUID CRYSTAL DISPLAY AND MANUFACTURING METHOD THEREOF

This application claims priority to and the benefit of Korean Patent Application No. 10-2015-0105257 filed in the Korean Intellectual Property Office on Jul. 24, 2015, the contents of which are incorporated herein in their entirety by reference.

BACKGROUND (a) Technical Field

The present disclosure relates to a liquid crystal display (LCD) and a manufacturing method thereof.

(b) Description of the Related Art

A liquid crystal display (LCD), which is currently one of the most widely used flat panel displays, includes two sheets of display panels formed with field generating electrodes such as a pixel electrode and a common electrode, and a liquid crystal (LC) layer interposed therebetween. The LCD displays an image by applying a voltage to the field generating electrodes to generate an electric field in the LC layer, determining directions of liquid crystals using the generated electric field, and controlling polarization of incident light.

In the LCD, to control liquid crystals to be tilted in a predetermined direction between the two display substrates, the liquid crystals should be aligned in a predetermined direction. A degree of uniformity in liquid crystal alignment is an important factor that determines the LCD's superior image quality.

Conventionally, the liquid crystals have been aligned by applying a polymer layer such as a polyimide on a substrate and then rubbing a surface of the substrate with a fiber such as nylon or polyester in a predetermined direction, thereby forming an alignment layer. However, when the surface is rubbed, fine dust may be present or static electricity may be generated due to friction between the fiber and the polymer layer, thereby causing critical problems when manufacturing the LCD.

To address problems associated with a contact type of method such as a rubbing method, research towards a contactless type of method such as a photoalignment method has recently been undertaken. In the photoalignment method, a polymer layer is irradiated with light, such as ultraviolet (UV) light, to induce anisotropy, thereby forming an alignment layer. According to the photoalignment method, transmittance, yield, contrast ratio, and the like properties of the LCD may be improved. However, photodecomposed units may remain and thus deteriorate LCD's characteristics.

Thus, there remains a need for a method capable of effectively removing decomposed units generated upon formation of the photoalignment layer.

The above information disclosed in this Background section is intended only to enhance the understanding of the background of the invention, and therefore, may contain information that does not form the prior art that is already known in this country or anywhere in the world to a person of ordinary skill in the art.

SUMMARY

The present disclosure has been made in an effort to provide a technique of effectively removing decomposed units which are generated when forming a photoalignment layer.

A manufacturing method of a liquid crystal display (LCD) according to an exemplary embodiment includes:
 applying a photoalignment agent on a substrate;
 baking the applied photoalignment agent;
 forming a photoalignment layer by irradiating the baked photoalignment agent with polarized light;
 baking the photoalignment layer; and
 removing at least one decomposed unit by cleaning the baked photoalignment layer using a cleaning solution including at least one of propylene glycol monomethyl ether, propylene glycol monomethyl ether acetate, or ethyl lactate.

The at least one decomposed unit may include at least one maleimide or at least one substituted maleimide, and at least one diamine may be combined with the maleimide or the substituted maleimide.

The at least one decomposed unit may include at least one of compounds represented by Chemical Formula (a) to Chemical Formula (g).

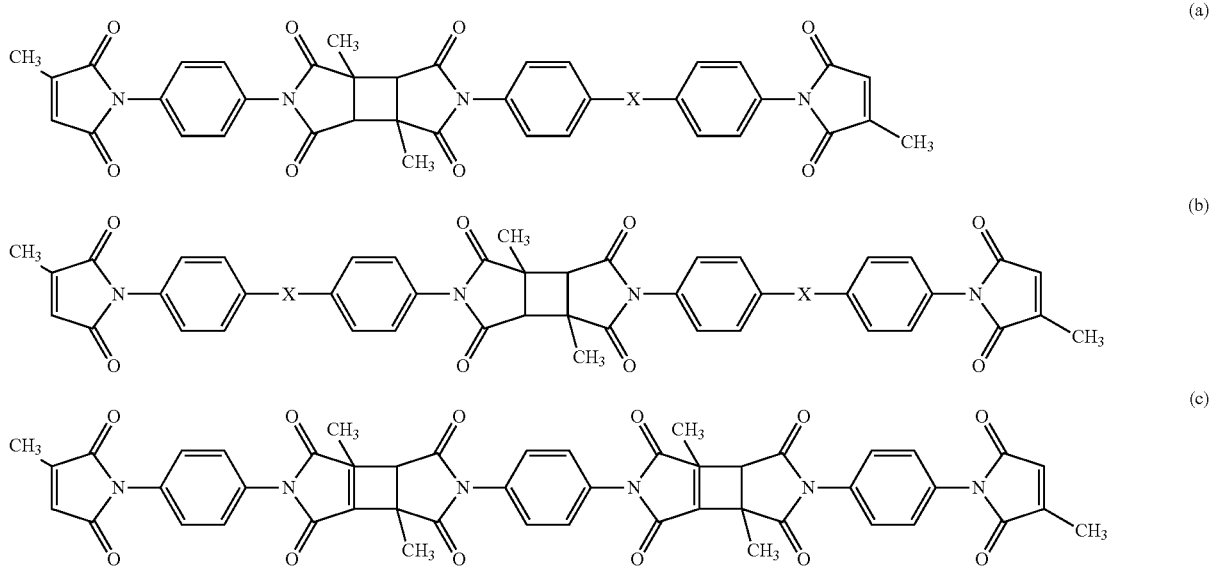

-continued

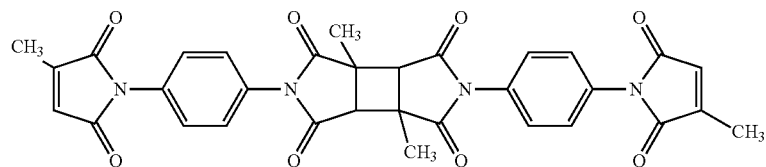
(d)

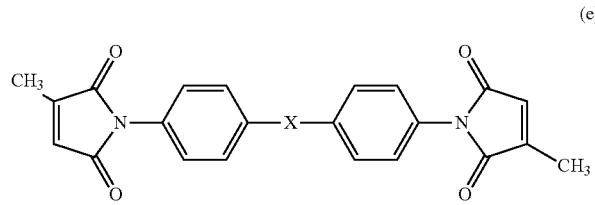
(e)

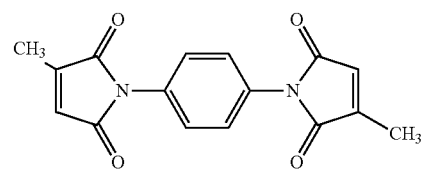
(f)

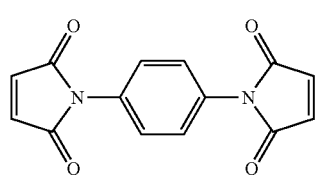
(g)

The photoalignment agent may include a copolymer of cyclobutane dianhydride and diamine and a copolymer of a substituted cyclobutane dianhydride and diamine.

The baking of the applied photoalignment agent may include prebaking and hard baking, and the copolymer of cyclobutane dianhydride and diamine and the copolymer of a substituted cyclobutane dianhydride and diamine may be phase separated by the prebaking.

The photoalignment layer may include a first layer adjacent to the substrate, and a second layer disposed on the first layer. The first layer may include a polyimide including a copolymer of cyclobutane dianhydride and a diamine, and the second layer may include a polyimide that includes a copolymer of a substituted cyclobutane dianhydride and a diamine.

The photoalignment layer may be formed as a single layer that includes a polyimide including a copolymer of a substituted CBDA and a diamine.

The polarized light may be ultraviolet light.

The propylene glycol monomethyl ether may include a compound represented by Chemical Formula 5.

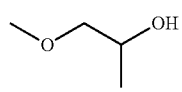
Chemical Formula 5

The propylene glycol monomethyl ether acetate may include a compound represented by Chemical Formula 6.

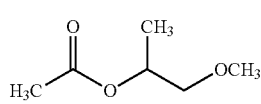
Chemical Formula 6

The ethyl lactate may include a compound represented by Chemical Formula 7.

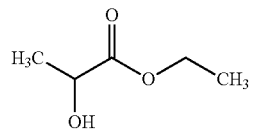
Chemical Formula 7

A manufacturing method of an LCD according to another exemplary embodiment includes:

applying a photoalignment agent on a substrate;

baking the applied photoalignment agent;

forming a photoalignment layer by irradiating the baked photoalignment agent with polarized light; and removing at least one decomposed unit by cleaning the photoalignment layer with a cleaning solution including propylene glycol monomethyl ether, propylene glycol monomethyl ether acetate, or both.

The manufacturing method may further include baking the photoalignment layer, prior to the removing of the at least one decomposed unit.

The at least one decomposed unit may include at least one maleimide or at least one substituted maleimide, and at least one diamine may be combined with the maleimide or the substituted maleimide.

The at least one decomposed unit may include compounds represented by Chemical Formula (a) to Chemical Formula (c).

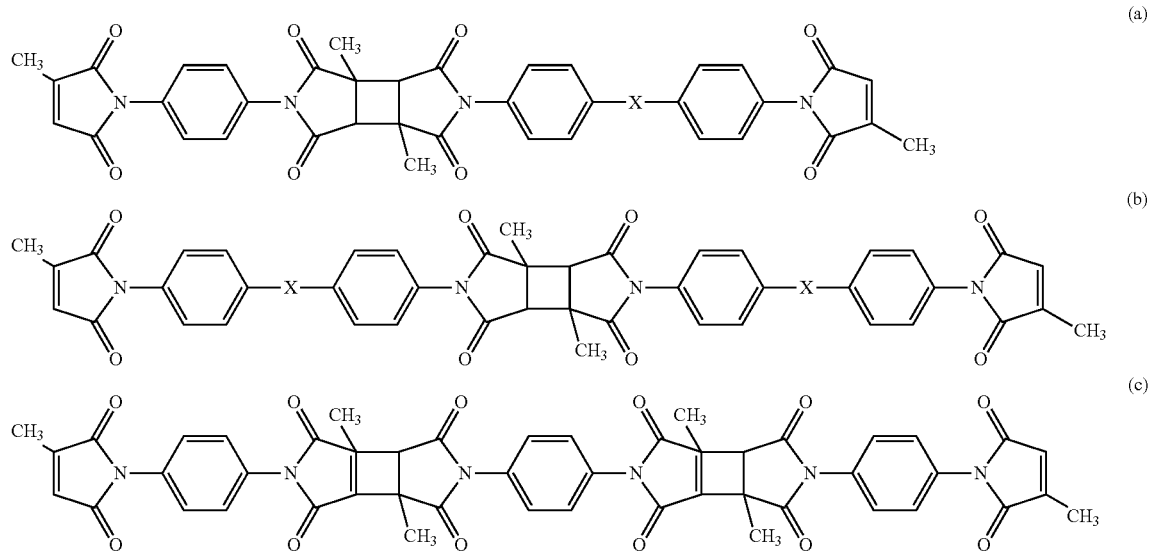

The photoalignment agent may include a copolymer of cyclobutane dianhydride and diamine, and a copolymer of a substituted cyclobutane dianhydride and diamine.

The baking of the applied photoalignment agent may include prebaking and hard baking, and the copolymer of cyclobutane dianhydride and diamine and the copolymer of a substituted cyclobutane dianhydride and diamine may be phase separated by the prebaking.

The photoalignment layer may include a first layer adjacent to the substrate, and a second layer disposed on the first layer. The first layer may include a polyimide including a copolymer of cyclobutane dianhydride and a diamine, and the second layer may include a polyimide including a copolymer of a substituted cyclobutane dianhydride and a diamine.

The photoalignment layer may be formed as a single layer that includes a polyimide including a copolymer of a substituted CBDA and a diamine.

According to the exemplary embodiment, the at least one decomposed unit may be selectively removed without deteriorating anisotropy. In addition, when removing the at least one decomposed unit according to the exemplary embodiment, the LCD may maintain a voltage holding ratio, surface energy of the alignment layer, and a thickness of the alignment layer, and particularly not causing a residual image to deteriorate.

BRIEF DESCRIPTION OF THE DRAWINGS

The above and other aspects, advantages, and features of this disclosure will become more apparent by describing in further detail exemplary embodiments thereof with reference to the accompanying drawings, in which:

FIG. 6 illustrates light leakage according to a cleaning agent according to an exemplary embodiment.

DETAILED DESCRIPTION

Figure 1:
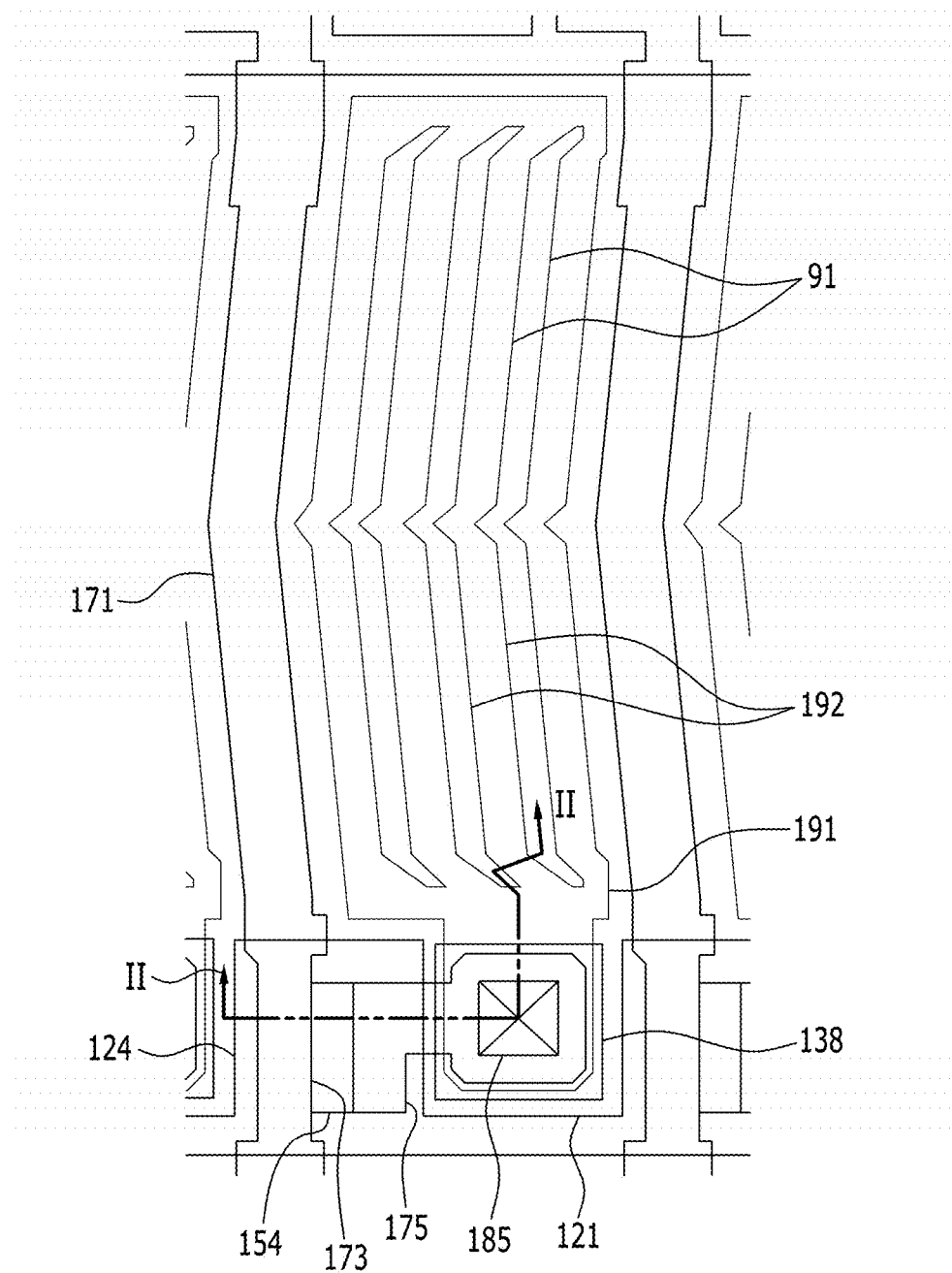
FIG. 1 is a top plan view of a liquid crystal display (LCD) according to an exemplary embodiment.

The present inventive concept will be described more fully hereinafter with reference to the accompanying drawings, in which exemplary embodiments of the invention are shown. Reference will be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Rather, these embodiments are provided so that this disclosure will be thorough and complete, and will fully convey the effects and features of the present disclosure and ways to implement the present disclosure will fully convey the concept of the invention to those skilled in the art. Accordingly, the exemplary embodiments are merely described below, by referring to the figures, to explain aspects. As those skilled in the art would realize, the described embodiments may be modified in various different ways, all without departing from the spirit or scope of the present disclosure. As used herein, the term "and/or" includes any and all combinations of one or more of the associated listed items. Expressions such as "at least one of," when preceding a list of elements, modify the entire list of elements and do not modify the individual elements of the list.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims. In the drawings, like reference numerals denote like elements throughout, and thus redundant description thereof will be omitted.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

As used herein, the terms such as "comprising", "including", "having", or the like are intended to indicate the existence of the features regions, integers, steps, operations, components, and/or elements disclosed in the specification, and are not intended to preclude the possibility that one or more other features or elements may exist or may be added.

In the drawings, the thickness of layers, films, panels, regions, etc. are enlarged or exaggerated for clarity. The size or thickness of each element shown in the drawings are arbitrarily illustrated for better understanding or ease of description, and thus the present disclosure is not limited thereto.

It will be understood that when an element such as a layer, film, region, or substrate is referred to as being "on" another element, it can be directly on the other element or intervening elements may also be present. In contrast, when an element is referred to as being "directly on" another element, there are no intervening elements present.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

A liquid crystal display (LCD) according to an exemplary embodiment and a manufacturing method thereof will be described in detail with reference to the drawings.

Figure 2:
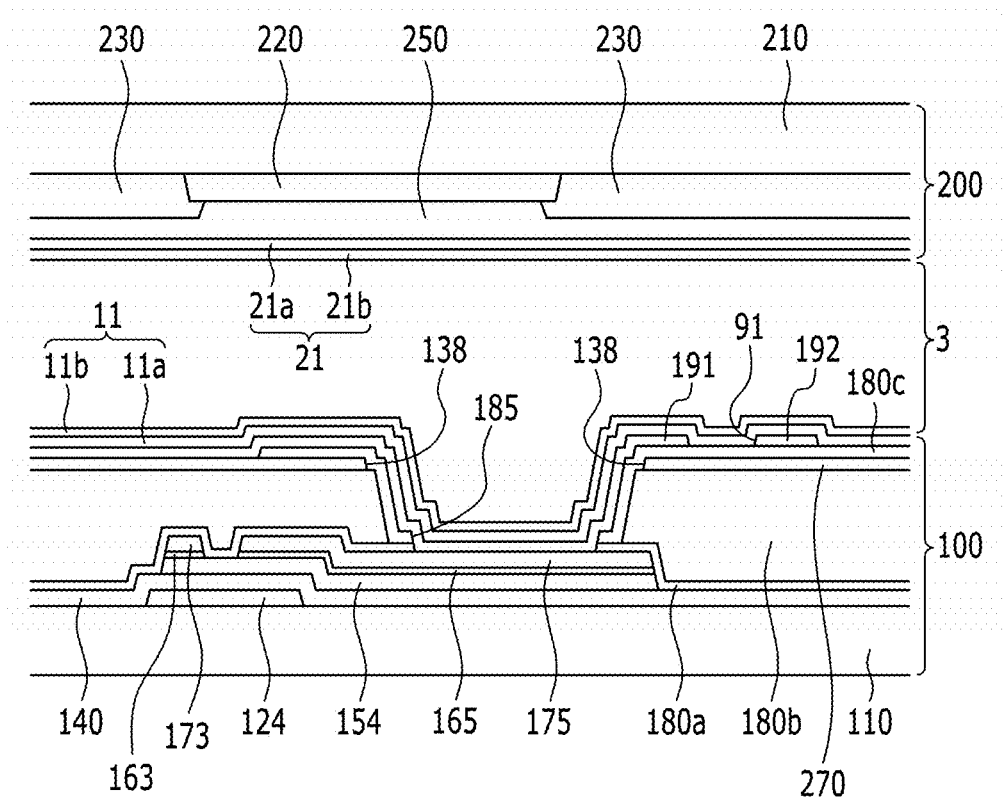
FIG. 2 is a cross-sectional view of FIG. 1 taken along the line II-II.

FIG. 1 is a top plan view of an LCD according to an exemplary embodiment, and FIG. 2 is a cross-sectional view of FIG. 1 taken along the line II-II.

Referring to FIGS. 1 and 2, the LCD according to the current exemplary embodiment includes lower and upper display substrates 100 and 200 facing each other, and a liquid crystal (LC) layer 3 interposed therebetween.

The lower display substrate 100 will be described first.

A gate conductor including a gate line 121 is formed on a lower substrate 110 that is made of transparent glass, plastic, etc.

The gate line 121 may include the gate electrode 124, and a wide end portion (not shown) to be coupled with another layer or an external driving circuit. The gate line 121 may be made of aluminum (Al) or an aluminum alloy, silver (Ag) or a silver alloy, copper (Cu) or a copper alloy, molybdenum (Mo) or a molybdenum alloy, or another metal such as chromium (Cr), tantalum (Ta), titanium (Ti), etc. The gate line 121 may be formed as a single conductive layer or a multilayer including at least two conductive layers having different physical properties.

A gate insulating layer 140 that is made of a silicon nitride (SiNx) or a silicon oxide (SiOx) is formed on the gate line 121. The gate insulating layer 140 may have a multilayer structure in which at least two insulating layers having different physical properties are included.

A semiconductor layer 154 that is made of amorphous silicon or polysilicon is formed on the gate insulating layer 140. The semiconductor layer 154 may also be formed as an oxide semiconductor.

Ohmic contacts 163 and 165 are formed on the semiconductor layer 154. The ohmic contacts 163 and 165 may be made of a material such as n+ hydrogenated amorphous silicon in which an n-type impurity such as phosphorus is doped at a high concentration, or of a silicide. The ohmic contacts 163 and 165 may be paired to be disposed on the semiconductor layer 154. When the semiconductor layer 154 is an oxide semiconductor, the ohmic contacts 163 and 165 may be omitted, and a barrier may be alternatively disposed.

A data line 171 including a source electrode 173 and a data conductor including a drain electrode 175 are formed on the ohmic contacts 163 and 165 and on the gate insulating layer 140.

The data line 171 may include a wide end portion (not shown) to be coupled with another layer or an external driving circuit. The data line 171 transmits a data signal, and substantially extends in a vertical direction to cross the gate line 121. In order to obtain maximum transmittance of the LCD, the data line 171 may have a portion that is curved, and the curved portion may substantially form a V-shape in the middle of a pixel area.

The source electrode 173 is a part of the data line 171, and is disposed on the same line as the data line 171. The drain electrode 175 is formed to extend in parallel with the source electrode 173. Accordingly, the drain electrode 175 may be formed in parallel with some of the data line 171. As a result, since a width of a thin film transistor may be increased even without increasing an area taken by the data conductor, an aperture ratio of the LCD can be increased.

The gate electrode 124, the source electrode 173, and the drain electrode 175 form one thin film transistor along with the semiconductor 154, and a channel of the thin film transistor is formed in a portion of the semiconductor layer 154 between the source electrode 173 and the drain electrode 175.

The data line 171 and the drain electrode 175 may be made of a refractory metal such as molybdenum, chromium, tantalum, titanium, etc., or an alloy thereof, and may have a multilayer structure in which a refractory metal layer (not shown) and a low resistance conductive layer (not shown) are included. Examples of the multilayer structure may include a double layer of a chromium or molybdenum lower layer and an aluminum upper layer, and a triple layer of a molybdenum lower layer, an aluminum middle layer, and a molybdenum upper layer. In addition, the data conductor may be made of various metals or conductors.

A first passivation layer 180a is formed on the data conductors 171, 173, and 175, the gate insulating layer 140, and an exposed portion of the semiconductor layer 154. The first passivation layer 180a may be made of an inorganic insulating material or the like. For example, the first passivation layer 180a may have a dual layer structure of a silicon oxide lower layer and a silicon nitride upper layer. The first passivation layer 180a may be made of an organic insulating material.

A second passivation layer 180b is formed on the first passivation layer 180a. The second passivation layer 180b may be made of an organic insulating material. The second passivation layer 180b may be a color filter. The second passivation layer 180b may uniquely exhibit one of primary colors if the second passivation layer 180b is a color filter. The primary colors may be, for example, three primary colors, such as red, green, and blue, or yellow, cyan, magenta, etc. Though not illustrated, an additional color filter for exhibiting mixed colors of the primary colors or white as well as the primary colors may be further included. If the second passivation layer 180b is the color filter, a color filter 230 may be omitted in the upper display substrate 200 to be described below. Unlike the current exemplary embodiment, the second passivation layer 180b may be made of an organic insulating material, and the color filter (not shown) may be formed between the first and second passivation layers 180a and 180b.

A common electrode 270 is formed on the second passivation layer 180b. The common electrode 270 may be formed as a whole plate on an entire surface of the substrate 110 while having a planar shape. That is, the common electrode 270 may have a plate-like planar shape. However, an opening 138 for coupling the pixel electrode 191 with the drain electrode 175 is disposed in a region of the common electrode 270 corresponding to a periphery of the drain electrode 175. The common electrode 270 may receive a constant common voltage that is supplied from outside of a display area.

An insulating layer 180c is formed on the common electrode 270. The insulating layer 180c may be made of an organic material or an inorganic insulating material.

A pixel electrode 191 is disposed on the insulating layer 180c. The pixel electrode 191 may include a curved edge that is nearly parallel to the curved portion of the data line 171. The pixel electrode 191 has a plurality of cutouts 91, and includes a plurality of branch electrodes 192 that are disposed between the neighboring cutouts 91.

A contact hole 185 exposing the drain electrode 175 is formed in the first passivation layer 180a, the second passivation layer 180b, and the insulating layer 180c. The pixel electrode 191 receives a data voltage from the drain electrode 175 while being physically and electrically connected to the drain electrode 175 via the contact hole 185.

A lower alignment layer 11 is formed on the pixel electrode 191 and on the insulating layer 180c. The lower alignment layer 11 includes a photoalignment layer.

The lower alignment layer 11 includes a polyimide that includes a repeating unit represented by Chemical Formula 1.

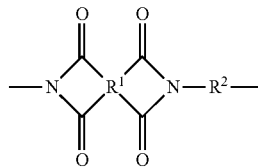

Chemical Formula 1

In Chemical Formula 1, $R^1$ is a tetravalent organic group derived from an aliphatic cyclic acid dianhydride or an aromatic acid dianhydride, and $R^2$ is a divalent organic group derived from an aromatic diamine.

The polyimide may include cyclobutane dianhydride (CBDA) represented by Chemical Formula 2 and/or a copolymer of a substituted CBDA represented by Chemical Formula 3 and a diamine.

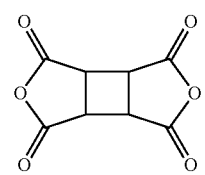

Chemical Formula 2

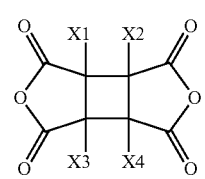

Chemical Formula 3

In Chemical Formula 3, X1, X2, X3, and X4 are independently hydrogen, a halogen, a C1-C30 substituted or unsubstituted alkyl group, a C6-C30 substituted or unsubstituted aryl group, or a substituted or unsubstituted C2-C30 heteroaryl group, and at least one of X1, X2, X3, and X4 is not hydrogen.

The C1-C30 alkyl group used in Chemical Formula 3 refers to a group derived from a saturated branched or non-branched (straight chain or linear) C1-C30 hydrocarbon. Detailed examples thereof may include a methyl group, an ethyl group, a propyl group, an iso-butyl group, a sec-butyl group, a tert-butyl group, a neo-butyl group, an iso-amyl group, and a hexyl group. At least one hydrogen in the C1-C30 alkyl group may be substituted with a substituent.

The C6-C30 aryl group used in Chemical Formula 3, refers to system containing at least one aromatic ring. The aromatic ring may be fused to another ring or may be non-fused. The aromatic ring may be linked to another ring (which may or may not be aromatic) through a single bond. Detailed examples thereof may include a phenyl group, a naphthyl group, and a tetrahydronaphthyl group.

The C3-C30 heteroaryl group used in Chemical Formula 3, refers to a group derived from an organic compound including at least one aromatic ring, wherein at least one carbon atom is replaced with a hetero atom selected from N, O, P, and S to form a heteroaromatic ring. The heteroaromatic ring may be fused to another ring or may be non-fused. The heteroaromatic ring may be linked to another ring (which may or may not be aromatic or heteroaromatic) through a single bond. Detailed example thereof may include a pyridyl group.

An alkyl group, an aryl group, and a heteroaryl group used in Chemical Formula 3 may include a "substituent" selected from a halogen atom, a C1-C20 alkyl group substituted with a halogen atom, such as $CCF_3$, $CHCF_2$, $CH_2F$, or $CCl_3$, a hydroxy group, a nitro group, a cyano group, an amino group, an amidino group, a hydrazine group, a hydrazone group, a carboxylic acid group or a salt thereof, a sulfonic acid group or a salt thereof, and a phosphoric acid group a salt thereof; or a "substituent" substituted with at least one selected from a C1-C20 alkyl group, a C2-C20 alkenyl group, a C2-C20 alkynyl group, a C3-C20 cycloalkyl group, a C6-C20 aryl group, a C6-C20 heteroaryl group, a C6-C20 aryl alkyl group, and a C6-C20 heteroaryl alkyl group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted C1-C30 alkyl" refers to a C1-C30 alkyl group substituted with C6-C20 aryl group, the total number of carbon atoms in the resulting aryl substituted alkyl group is C7-C50.

For example, the substituted CBDA may include a compound represented by Chemical Formula 3-1.

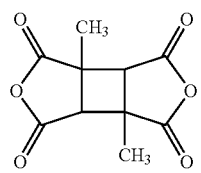

Chemical Formula 3-1

The diamine may include a compound represented by Chemical Formula 4 and/or Chemical Formula 5.

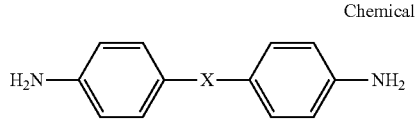

Chemical Formula 4

In Chemical Formula 4, X is

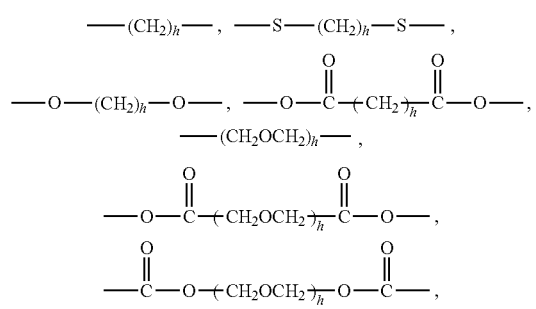

—continued $$—O—(CH_2OCH_2)_h—O—,$$

$$—\overset{O}{\underset{\|}{C}}—O—(CH_2)_h—O—\overset{O}{\underset{\|}{C}}—,$$

$$—(CH_2)_{h1}—O—(CH_2)_{h2}—, \text{ or}$$

$$—(CH_2)_{h1}\overset{O}{\underset{\|}{C}}—O—(CH_2)_{h2}—,$$

where h is a natural number of 1 to 10, and h1 and h2 are natural numbers selected so that the sum of carbon numbers of the alkylene group of X may be 2 to 10.

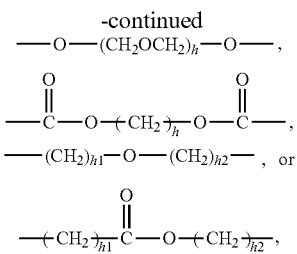

Chemical Formula 5

The diamine is not limited to compounds represented by Chemical Formulae 4 and 5, and may include, for example, a compound of Chemical Formula 5 where hydrogen connected to a carbon ring is substituted with an alkyl group, a halogen, sulfur, etc., and a diamine commonly used in a polyimide synthesis. In addition, the diamine may include an aromatic diamine such as p-phenylenediamine, m-phenylenediamine, 2,5-diaminotoluene, 2,6-diaminotoluene, 4,4'-diaminobiphenyl, 3,3'-dimethyl-4,4'-diaminobiphenyl, 3,3'-dimethoxy-4,4'-diaminobiphenyl, diaminodiphenylmethane, diaminodiphenylether, 2,2'-diaminodiphenylpropane, bis(3,5-diethyl-4-aminophenyl)methane, diaminodiphenylsulfone, diaminobenzophenone, diaminonaphthalene, 1,4-bis(4-aminophenoxy)benzene, 1,4-bis(4-aminophenyl)benzene, 9,10-bis(4-aminophenyl)anthracene, 1,3-bis(4-aminophenoxy)benzene, 4,4'-bis(4-aminophenoxy)diphenylsulfone, 2,2-bis[4-(4-aminophenoxy)phenyl]propane, 2,2-bis(4-aminophenyl)hexafluoropropane, and 2,2-bis[4-(4-aminophenoxy)phenyl]hexafluoropropane; an alicyclic diamine such as bis(4-aminocyclohexyl)methane, bis(4-amino-3-methylcyclohexyl)methane, and the like; and a aliphatic diamine such as tetramethylenediamine, hexamethylenediamine, and the like.

The lower alignment layer 11 may have a dual layer structure of a first alignment layer 11a and a second alignment layer 11b. In this case, the lower first alignment layer 11a may primarily include a polyimide including a copolymer of CBDA and a diamine, and in the upper second alignment layer 11b, $R^1$ may primarily include a polyimide that includes a copolymer of a substituted CBDA and a diamine. In some exemplary embodiments, the lower alignment layer 11 may have a single layer structure. In this case, the lower alignment layer 11 may primarily include a polyimide including a copolymer of a substituted CBDA and a diamine.

The upper display substrate 200 will now be described.

A light blocking member 220 is formed on an upper substrate 210 that is made of transparent glass or plastic. The light blocking member 220 is also called a black matrix, and serves to prevent light leakage.

A color filter 230 is formed on the upper substrate 210. When the second passivation layer 180b of the lower panel 100 is the color filter or when the color filter is formed in the lower display substrate 100, the color filter 230 of the upper panel 200 may be omitted. In addition, the light blocking member 220 of the upper display substrate 200 may also be formed on the lower display substrate 100.

An overcoat 250 is formed on the color filter 230 and on the light blocking member 220. The overcoat 250 may be made of an organic insulating material, and serves to prevent exposure of the color filter 230 and to provide a smooth surface. The overcoat 250 may be omitted.

An upper alignment layer 21 is formed on the overcoat 250. The upper alignment layer 21 may be made of the same material as the lower alignment layer 11 described above. The upper alignment layer 21 may have a dual layer structure of a first alignment layer 21a and a second alignment layer 21b as has the lower alignment layer 11, or may have a single layer structure. In the dual layer structure, the first alignment layer 21a may primarily include a polyimide that includes a copolymer of BDA and a diamine, and the second alignment layer 21b may primarily include a polyimide that includes a copolymer of a substituted CBDA and a diamine. In the single layer structure, the upper alignment layer 21 may primarily include a copolymer of a substituted CBDA and a diamine.

The LC layer 3 may include liquid crystals having negative dielectric anisotropy or positive dielectric anisotropy. The liquid crystals of the LC layer 3 may be arranged such that their long axes are parallel to the display substrates 100 and 200.

The pixel electrode 191 receives the data voltage from the drain electrode 175, and the common electrode 270 receives the constant common voltage from a common voltage application unit that is disposed outside the display area. Then, the pixel electrode 191 and the common electrode 270 generate an electric field, and the liquid crystals of the LC layer 3 disposed on the two electrodes 191 and 270 may rotate in a direction that is parallel to the generated electric field. Depending on the rotating direction of LC molecules determined as such, polarization of light transmitted through the LC layer varies. The pixel electrode 191 and the common electrode 270 are also called field generating electrodes since they generate the electric field.

In the LCD according to the illustrated exemplary embodiment, the common electrode 270 has a flat planar shape, and the pixel electrode 191 has a plurality of branch electrodes. In an LCD according to another exemplary embodiment, a pixel electrode 191 may have a flat planar shape, and a common electrode 270 may have a plurality of branch electrodes.

A manufacturing method of an LCD based on a process of forming a photoalignment layer will now be described with reference to FIGS. 3 to 5. In the LCD, components other than a photoalignment layer may be formed by various methods, so a detailed description thereof will be omitted.

Figure 3:
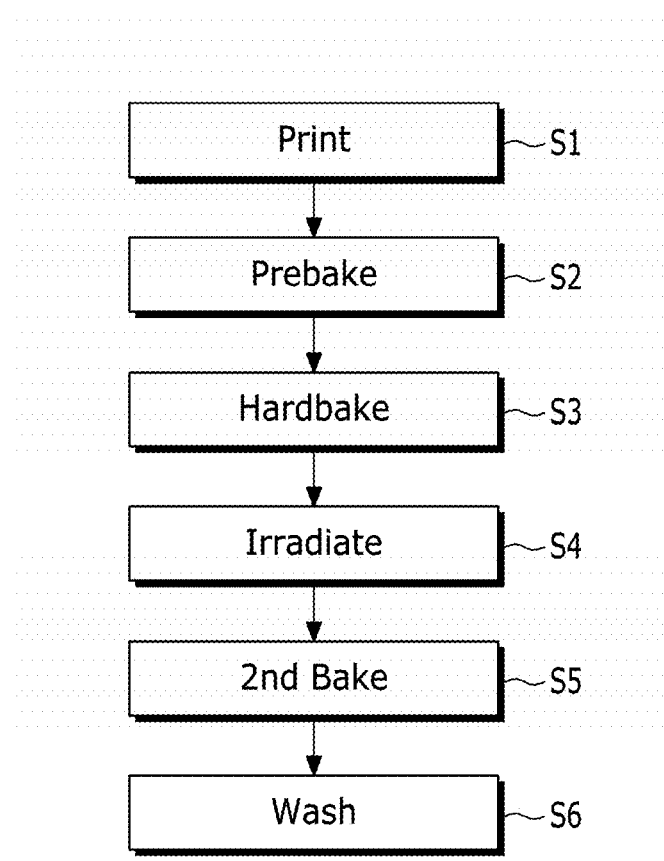
FIG. 3 is a flowchart showing a process of forming a photoalignment layer according to an exemplary embodiment.

FIG. 3 is a flowchart showing a process of forming a photoalignment layer according to an exemplary embodiment. FIG. 4 is a structural formula showing decomposition of a polyimide in the photoalignment layer according to an exemplary embodiment, and FIG. 5 illustrates a process of changing from isotropy to anisotropy in the photoalignment layer according to the exemplary embodiment.

Referring to FIG. 3, formation of the photoalignment layer includes printing S1, prebaking S2, hard baking S3, irradiating S4, second baking S5, and washing S6. In this case, the photoalignment layer may correspond to the lower alignment layer 11 and the upper alignment layer 21 of the LCD that are described with reference to FIGS. 1 and 2.

First, the printing S1 includes applying a photoalignment agent solution on a substrate in which a pixel electrode and the like are formed. In this case, a photoalignment agent may include CBDA and/or a copolymer of a substituted CBDA and a diamine. For example, the photoalignment agent may include a copolymer of CBDA and a diamine and a copolymer of a substituted CBDA and a diamine. In some embodiments, the photoalignment agent may not include CBDA. The photoalignment agent may include CBDA and a copolymer of a substituted CBDA and a diamine. The applying of the photoalignment agent may be performed using a printing method or an inkjet method.

In the prebaking S2, the copolymer of CBDA and a diamine included in the photoalignment agent moves toward the substrate due to their different polarities, causing the copolymer of CBDA and a diamine and the copolymer of a substituted CBDA and a diamine to be phase separated and causing the solvent to evaporate. In the hard baking S3, since the photoalignment agent is imidized, a polyimide including the copolymer of CBDA and a diamine is formed in the first layer close to the substrate, and a polyimide including the copolymer of a substituted CBDA and a diamine is formed in a second layer disposed on the first layer. Though made of different materials, the first and second layers may not be clearly identified since they are not separately formed but a mixture of them is phase separated. For example, a boundary between the first layer and the second layer may be gradually identified, the material included in the second layer may be present in the first layer, and the material included in the first layer may be present in the second layer.

In the irradiating S4, polarized light is irradiated to the photoalignment agent that is imidized via the prebaking and hard baking, thereby forming a photoalignment layer. Ultraviolet (UV) light having a wavelength range of about 240 nanometers (nm) to about 380 nm may be irradiated, and particularly, UV light of about 245 nm may be irradiated. The polarized UV light may include energy ranging from about 0.20 Joules per square centimeter ($J/cm^2$) to 1.0 $J/cm^2$, particularly, energy ranging from 0.40 $J/cm^2$ to 0.50 $J/cm^2$. A polarization direction of the UV light may be perpendicular to an alignment direction.

Figure 4:
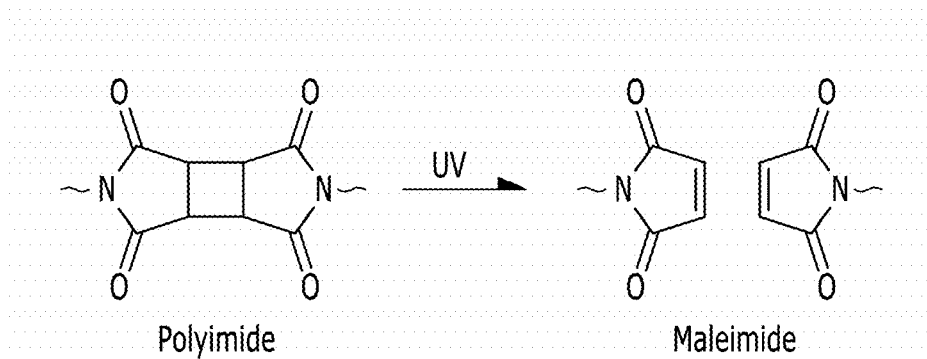
FIG. 4 is a structural formula illustrating decomposition of a polyimide in the photoalignment layer according to an exemplary embodiment.
Figure 5:
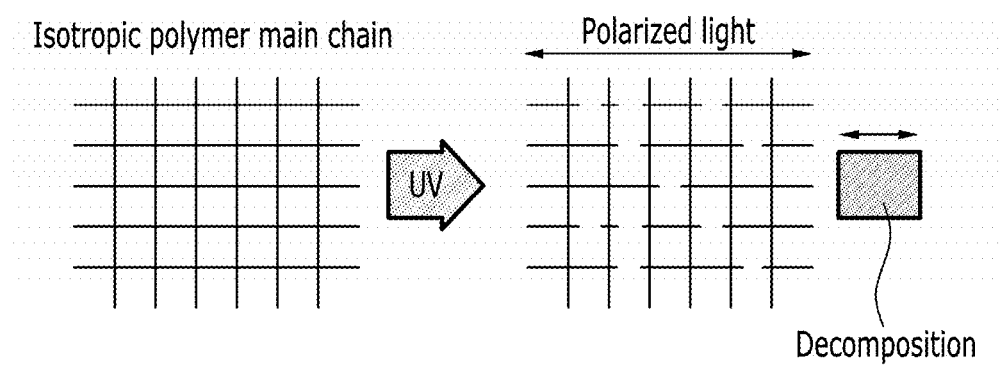
FIG. 5 illustrates a process of changing from isotropy to anisotropy in the photoalignment layer according to an exemplary embodiment.

Referring to FIGS. 4 and 5, the forming of the photoalignment layer will be described in more detail. Referring to FIG. 4, when the UV light is irradiated to a polyimide including the copolymer of CBDA and a diamine, photodecomposition occurs to form a maleimide. FIG. 5 illustrates that a polymer main chain including a polyimide illustrated in FIG. 4 is decomposed and aligned as the polarized UV light is irradiated. Referring to FIG. 5, when the polarized UV light is irradiated to an isotropic polymer main chain, photodecomposition may occur in the polarization direction (absorption axis direction) such that the photoalignment layer is formed to have the alignment direction perpendicular to the polarization direction. In this case, when an amount of exposure is too small, the alignment tendency may deteriorate since a decomposition rate is low. On the contrary, when the amount of exposure increases too much, the alignment tendency may deteriorate since the decomposition rate increases and decomposition occurs in other directions as well as in the polarization direction. A polyimide including the copolymer of CBDA and a diamine is illustrated as an example, but such a mechanism of forming the photoalignment layer may be identically applicable to a polyimide including the copolymer of a substituted CBDA and a diamine.

Referring back to FIG. 3, the second baking S5 is performed to maximize the alignment tendency. Since the photoalignment layer is baked once again, photodecomposed molecules may be rearranged to increase anisotropy.

When the photoalignment layer is formed by the irradiating S4, at least one decomposed unit is generated. The at least one decomposed unit may include a maleimide or a substituted maleimide. At least one diamine and at least one dianhydride may be combined in the at least one decomposed unit. Examples of the at least one decomposed unit may include chemical compounds that are represented by Chemical Formula (a) to Chemical Formula (g).

ment layer. Accordingly, the washing S6 for removing the decomposed units using a cleaning agent as a solvent is performed.

In the washing S6, at least one of propylene glycol monomethyl ether (PGME), propylene glycol monomethyl ether acetate (PGMEA), and ethyl lactate (EL) may be used as the cleaning agent.

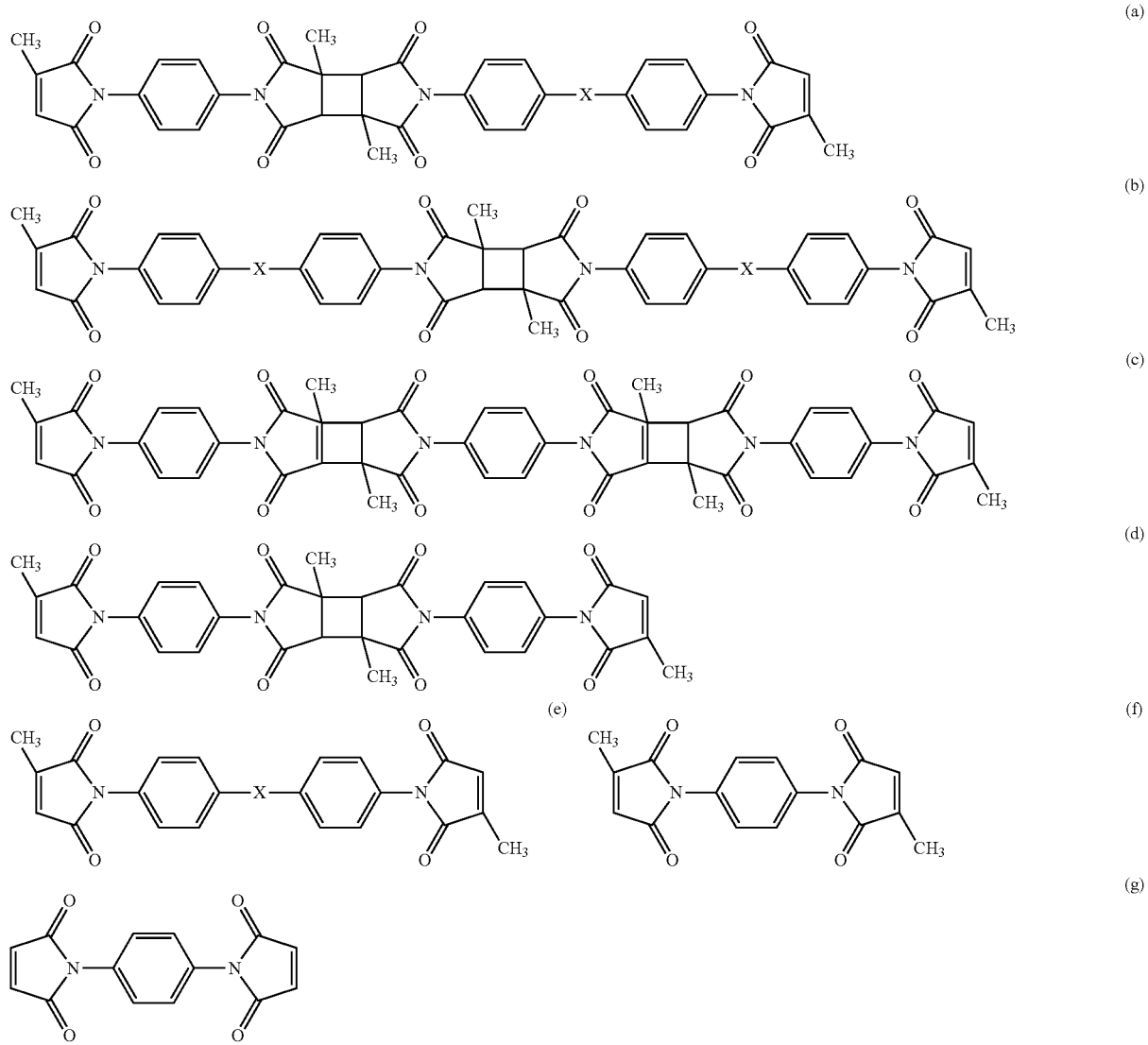

The decomposed units described above may cause, for example, alignment defects, thereby causing light leakage. Some of decomposed units having comparably smaller molecular weights may be partially evaporated and removed during the second baking S5. However, since decomposed units having comparably greater molecular weights, which are, for example, represented by Chemical Formula (a) to Chemical Formula (c), are difficult to remove though they are processed under the second baking S5, a considerable amount of the decomposed units remain in the photoalign- PGME may include a compound represented by Chemical Formula 5.

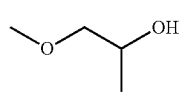

Chemical Formula 5

PGMEA may include a compound represented by Chemical Formula 6.

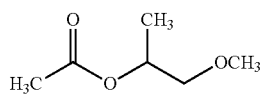

Chemical Formula 6

EL may include a compound represented by Chemical Formula 7.

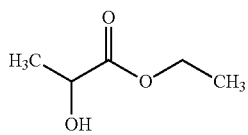

Chemical Formula 7

In addition, each of derivatives of PGME, PGMEA, and EL described above may be used as the cleaning agent. For example, the PGME derivative may include a compound represented by Chemical Formula 8.

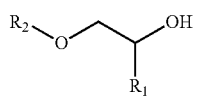

Chemical Formula 8

In Chemical Formula 8, R1 is an alkyl group having 1 to 4 carbon atoms, and R2 is an alkyl group having 1 to 3 carbon atoms.

The cleaning agents described above may be selected depending on the decomposed units and a solubility parameter of the cleaning solution. For example, as a difference in solubility parameters between the cleaning agents and the decomposed units, the cleaning solution shows excellent removal of the decomposed units. In Table 1 below, in addition to the cleaning agent such as PGME, PGMEA, and EL described above, a solubility parameter of IPA (isopropyl alcohol) and solubility parameters of the decomposed units are shown for comparison.

TABLE 1

| | | Solubility Parameter (MPa)$^{0.5}$ | |
|---|---|---|---|
| | | Documented value | Calculated value |
| Cleaning agent | PGME | 21.9 | 22.4 |
| | PGMEA | 19.3 | 19.3 |
| | EL | 21.7 | 21.0 |
| | IPA | 24.0 | 23.6 |
| Decomposed unit | Chemical Formula (a) | — | 22.0 |
| | Chemical Formula (b) | — | 18.3 |
| | Chemical Formula (c) | — | 22.1 |

As described above, in the current exemplary embodiment, the washing S6 is performed after the second baking S5. A photoalignment layer is stabilized since it is highly imidized by the second baking, and anisotropy of the photoalignment layer may be maintained by performing the washing after the second baking. In addition, since the decomposed units vaporized during the second baking and trapped inside an oven may transfer (drop) again onto the substrate and contaminate the photoalignment layer, it is effective to remove the decomposed units when performing the washing after the second baking. On the contrary, when the washing is performed before the second baking, the photoalignment layer may have deteriorated anisotropy since it is less stabilized, and may be contaminated by the decomposed units inside the oven. However, the present inventive concept does not exclude performing the washing before the second baking, and in some embodiments, the second baking may be performed after the washing or may be omitted. Even if the washing is performed before the second baking, the cleaning agent according to the current exemplary embodiment is selected in such a way that it has an acceptable degree of effect on the non-decomposed main chain of the photoalignment layer.

The substrate formed with the photoalignment layer is washed using the cleaning agents, respectively, indicated by Table 1, before and after the second baking, and characteristics of the LCD and the photoalignment layer are shown in Table 2 below.

TABLE 2

| | Cleaning agent | VHR (1 Hz @ 60° C.) | Surface energy (%) | Thickness (Å) | Residual image (naked eye) |
|---|---|---|---|---|---|
| Washing after second baking | PGME | 98.6 | 57 | 730 | 1.5 |
| | PGMEA | 98.6 | 55 | 725 | 1.6 |
| | EL | 98.5 | 56 | 725 | 1.7 |
| | IPA | 98.5 | 56 | 730 | 1.8 |
| Second baking after washing | PGME | 98.8 | 56 | 710 | 1.8 |
| | PGMEA | 98.5 | 54 | 705 | 1.7 |
| | EL | 98.5 | 56 | 710 | 1.8 |
| | IPA | 98.3 | 55 | 725 | 1.8 |

Referring to Table 2, voltage holding ratios and surface energy when performing the washing before and after the second baking show quite similar results. However, a thickness of the photoalignment layer when performing the washing after the second bake, is shown to be thicker by 15 to 20 Angstroms (Å) than a thickness of the photoalignment layer when performing the washing before the second baking. This is because the second baking may improve stability of the photoalignment layer. The reduced thickness of the photoalignment layer represents a decrease in the alignment tendency. All results are acceptable in terms of degrees of a residual image, but performing the washing after the second baking shows much better results.

Now, evaluation results regarding occurrence of light leakage in the LCD will be described when the washing is performed using the cleaning agent described above.

FIG. 6 illustrates generation of light leakage according to cleaning agents.

Referring to FIG. 6, high temperature storage (HTS) evaluation results for the LCD to which the washing is performed using the cleaning agents (PGME, PGMEA, and EL) according to the current exemplary embodiment and the control cleaning agent (IPA) are shown. The washing is performed after the second baking, and the second baking is performed for 15 minutes (min) and 30 min at temperatures of 220° C. and 230° C., respectively. When the washing is performed using PGME, PGMEA, and EL, all samples do not show any light leakage at all even after 500 hours (h) have passed. On the contrary, when the washing is performed using IPA, a sample to which the second baking is performed for 15 min shows extensive light leakage from the start, and a sample to which the second baking is performed for 30 min shows light leakage after 24 h have passed. Accordingly, PGME, PGMEA, and EL are all excellent in their capabilities of removing the decomposed units.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A manufacturing method of a liquid crystal display, comprising:
applying a photoalignment agent on a substrate, wherein the photoalignment agent comprises a copolymer of cyclobutane dianhydride and a diamine and a copolymer of a substituted cyclobutane dianhydride and a diamine;
baking the applied photoalignment agent;
forming a photoalignment layer by irradiating the baked photoalignment agent with polarized light;
baking the photoalignment layer; and
removing at least one decomposed unit by cleaning the baked photoalignment layer using a cleaning solution comprising at least one of propylene glycol monomethyl ether, propylene glycol monomethyl ether acetate, or ethyl lactate, wherein the baking of the applied photoalignment agent comprises prebaking and hard baking, and wherein the copolymer of cyclobutane dianhydride and a diamine and the copolymer of a substituted cyclobutane dianhydride and a diamine are phase separated by the prebaking.

2. The manufacturing method of claim 1, wherein the at least one decomposed unit comprises at least one maleimide or at least one substituted maleimide, and wherein at least one diamine is combined with the maleimide or the substituted maleimide.

3. The manufacturing method of claim 2, wherein the at least one decomposed unit comprises at least one of compounds represented by Chemical Formula (a) to Chemical Formula (g):

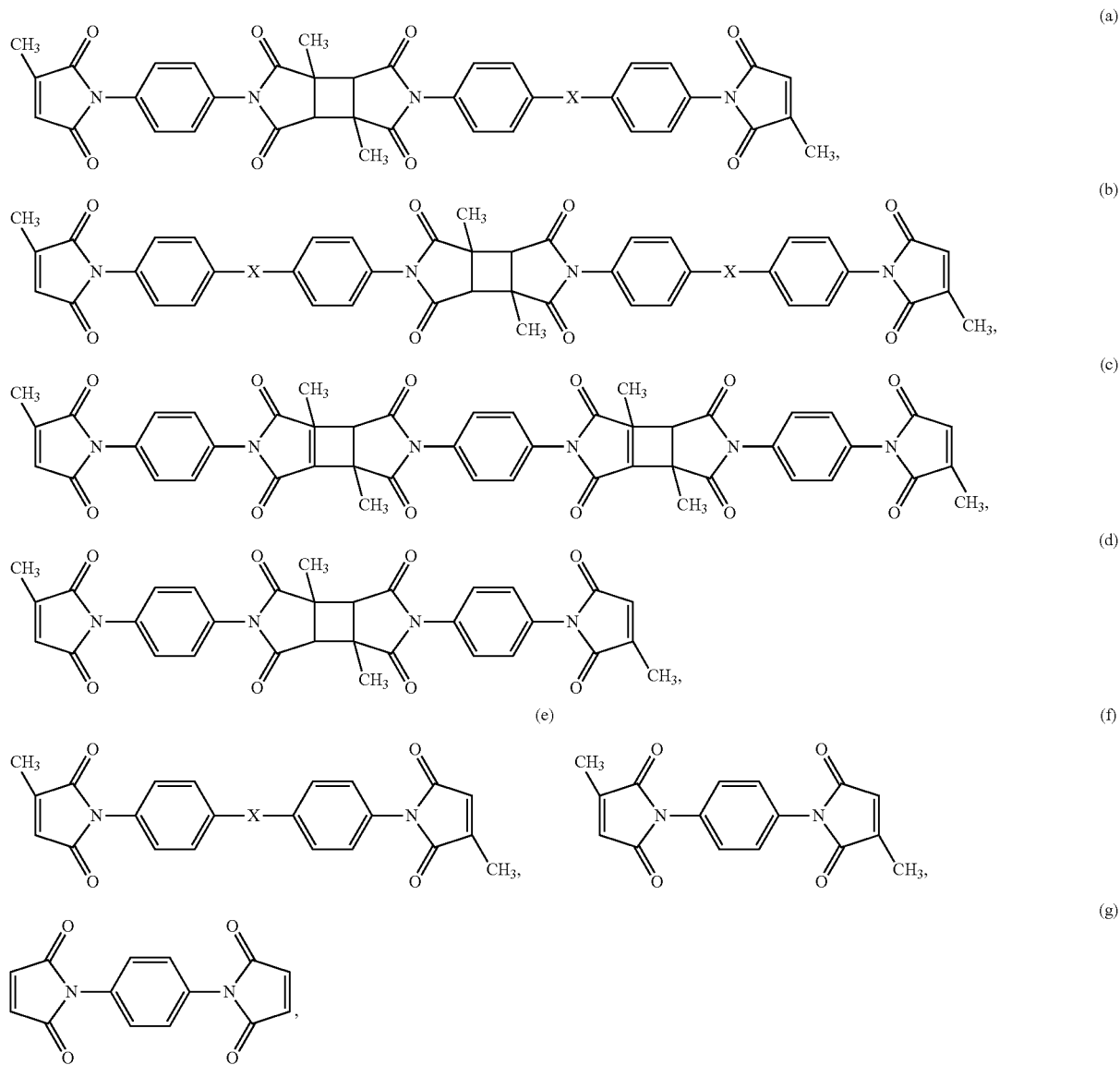

wherein X is —(CH2)$_h$—, —S—(CH2)$_h$-S—, —O—(CH2)$_h$-O—,

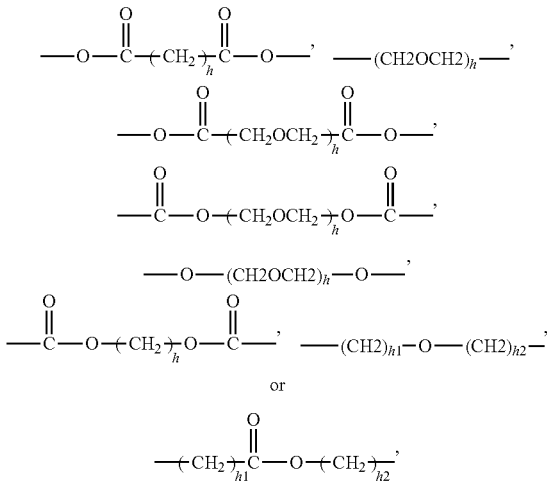

where h is a natural number of 1 to 10, and h1 and h2 are natural numbers selected so that the sum of carbon numbers of the alkylene group of X may be 2 to 10.

4. The manufacturing method of claim 3, wherein the at least one decomposed unit comprises at least one of the compounds represented by Chemical Formula (a) to Chemical Formula (c):

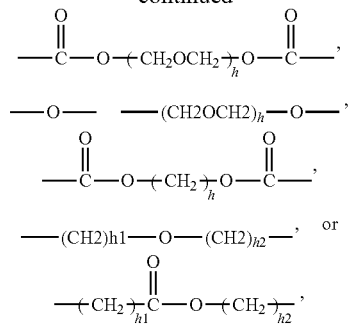

where h is a natural number of 1 to 10, and h2 is a natural number selected so that the sum of carbon numbers of the alkylene group of X may be 2 to 10.

5. The manufacturing method of claim 1, wherein the photoalignment layer comprises a first layer adjacent to the substrate and a second layer disposed on the first layer, wherein
the first layer comprises a polyimide comprising a copolymer of cyclobutane dianhydride and a diamine, and
the second layer comprises a polyimide comprising a copolymer of a substituted cyclobutane dianhydride and a diamine.

6. The manufacturing method of claim 1, wherein the photoalignment layer is formed as a single layer that comprises a polyimide comprising a copolymer of a substituted cyclobutane dianhydride and a diamine.

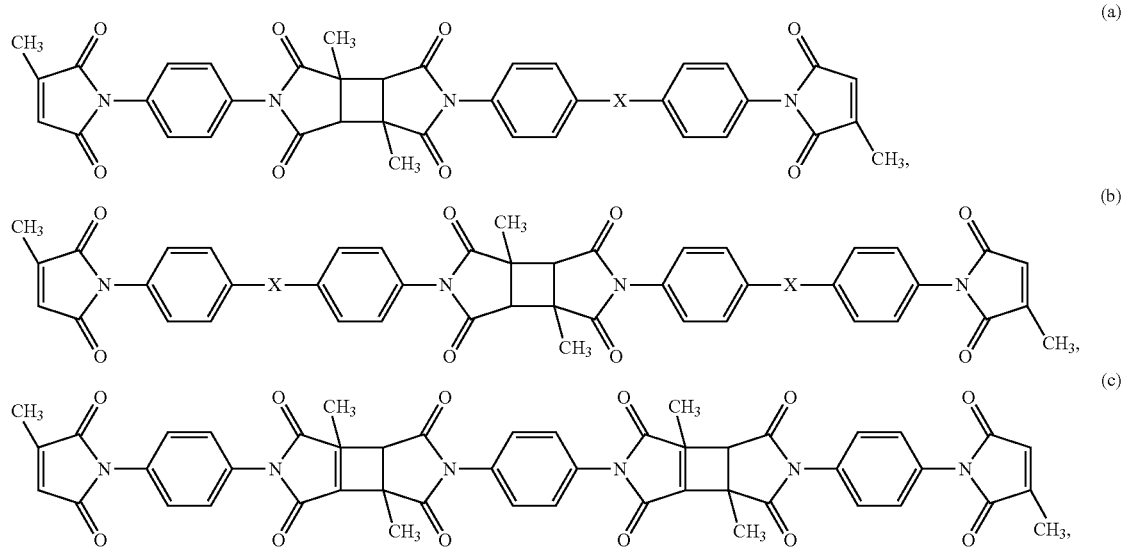

wherein X is

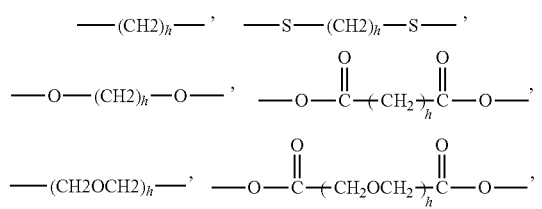

7. The manufacturing method of claim 1, wherein the polarized light is ultraviolet light.

8. The manufacturing method of claim 1, wherein the propylene glycol monomethyl ether comprises a compound represented by Chemical Formula 5:

Chemical Formula 5

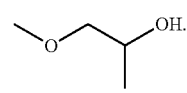

9. The manufacturing method of claim 1, wherein the propylene glycol monomethyl ether acetate comprises a compound represented by Chemical Formula 6:

Chemical Formula 6

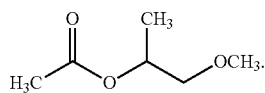

10. The manufacturing method of claim 1, wherein the ethyl lactate comprises a compound represented by Chemical Formula 7:

Chemical Formula 7

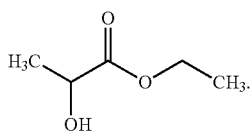

11. A manufacturing method of a liquid crystal display, comprising:
applying a photoalignment agent on a substrate, wherein the photoalignment agent comprises a copolymer of cyclobutane dianhydride and a diamine, and a copolymer of a substituted cyclobutane dianhydride and a diamine;
baking the applied photoalignment agent;
forming a photoalignment layer by irradiating the baked photoalignment agent with polarized light; and
removing at least one decomposed unit by cleaning the photoalignment layer with a cleaning solution comprising propylene glycol monomethyl ether, propylene glycol monomethyl ether acetate, or both, wherein the baking of the applied photoalignment agent comprises prebaking and hard baking, and wherein the copolymer of cyclobutane dianhydride and a diamine and the copolymer of substituted cyclobutane dianhydride and a diamine are phase separated by the prebaking.

12. The manufacturing method of claim 11, further comprising baking the photoalignment layer prior to the removing of the at least one decomposed unit.

13. The manufacturing method of claim 11, wherein the at least one decomposed unit comprises at least one maleimide or at least one substituted maleimide, and wherein at least one diamine is combined with the maleimide or the substituted maleimide.

14. The manufacturing method of claim 13, wherein the at least one decomposed unit comprises at least one of compounds represented by Chemical Formula (a) to Chemical Formula (c):

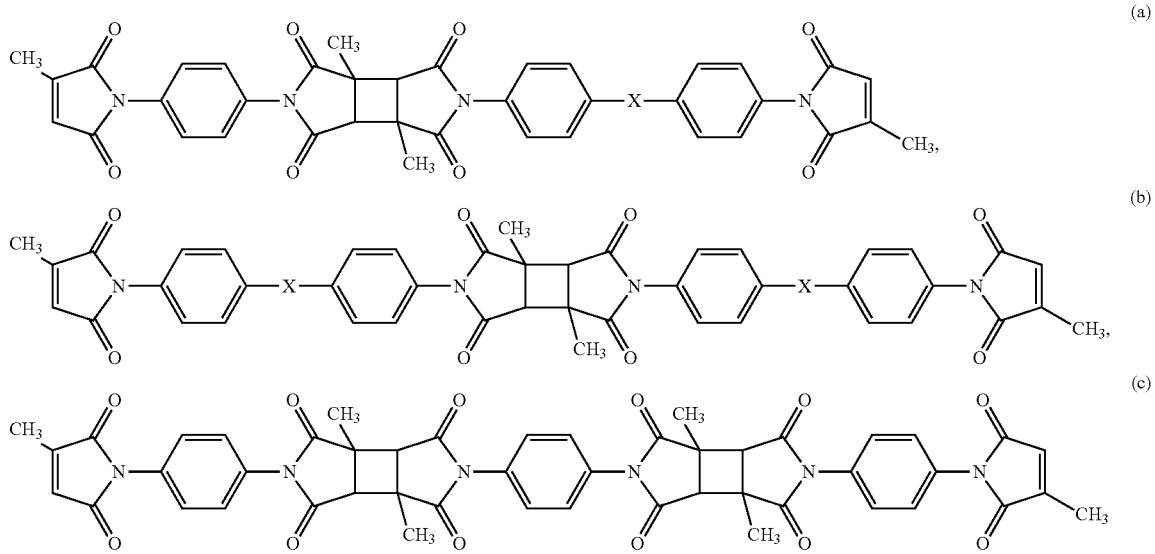

wherein X is

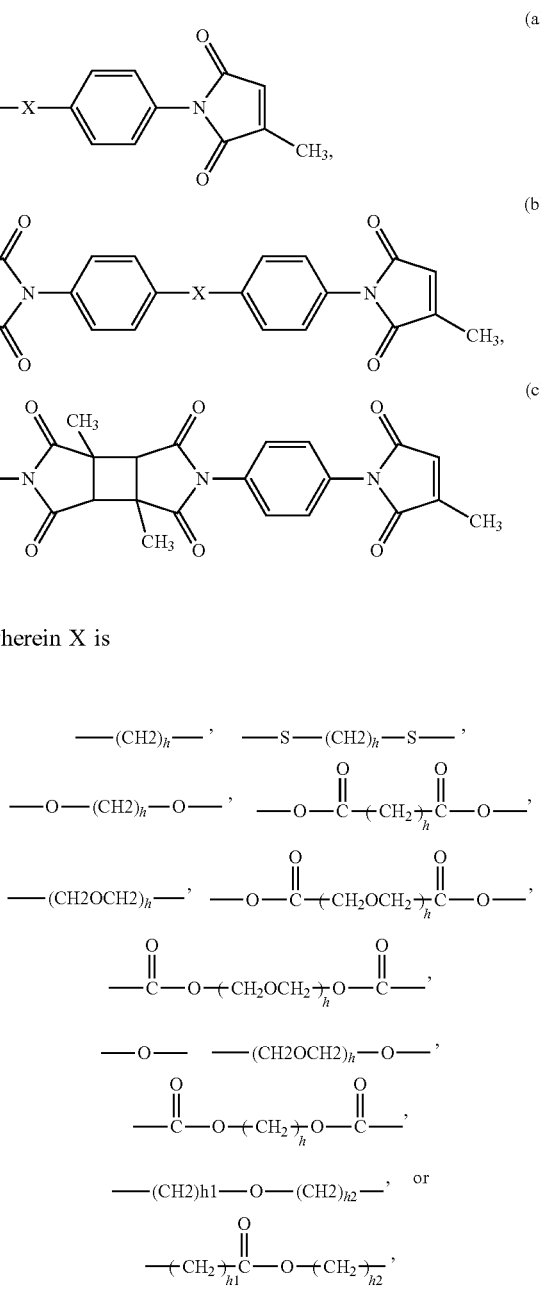

where h is a natural number of 1 to 10, and h2 is a natural number selected so that the sum of carbon numbers of the alkylene group of X may be 2 to 10.

15. The manufacturing method of claim 11, wherein the photoalignment layer comprises a first layer adjacent to the substrate and a second layer disposed on the first layer, wherein
   the first layer comprises a polyimide comprising a copolymer of cyclobutane dianhydride and a diamine, and
   the second layer comprises a polyimide comprising a copolymer of a substituted cyclobutane dianhydride and a diamine.

16. The manufacturing method of claim 11, wherein the photoalignment layer is formed as a single layer that comprises a polyimide including a copolymer of a substituted cyclobutane dianhydride and a diamine.

* * * * *